(12) United States Patent
Heaton et al.

(10) Patent No.: US 7,811,235 B2
(45) Date of Patent: Oct. 12, 2010

(54) AERODYNAMIC TISSUE DRIVER

(75) Inventors: James Tracey Heaton, Mansfield, MA (US); James B. Kobler, Andover, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 1416 days.

(21) Appl. No.: 10/964,373

(22) Filed: Oct. 13, 2004

(65) Prior Publication Data

US 2006/0079737 A1  Apr. 13, 2006

(51) Int. Cl.
*A61B 5/00* (2006.01)

(52) U.S. Cl. ..................................................... 600/552

(58) Field of Classification Search ......... 600/185–200, 600/552, 127, 129, 156
See application file for complete search history.

(56) References Cited

U.S. PATENT DOCUMENTS

| | | | | |
|---|---|---|---|---|
| 2,187,757 A | * | 1/1940 | Scrimgeour | 76/105 |
| 2,859,515 A | * | 11/1958 | Kinman | 30/141 |
| 4,840,173 A | | 6/1989 | Porter, III | |
| 4,995,388 A | * | 2/1991 | Brain | 128/207.15 |
| 5,651,761 A | * | 7/1997 | Upsher | 600/194 |
| 5,893,830 A | * | 4/1999 | Zeitels | 600/190 |
| 6,159,243 A | | 12/2000 | Schouwenburg | |
| 6,390,093 B1 | | 5/2002 | Mongeon | |
| 6,526,977 B1 | | 3/2003 | Goebel | |
| 6,666,819 B2 | | 12/2003 | Heine et al. | |
| 6,734,893 B1 | * | 5/2004 | Hess et al. | 348/68 |
| 6,843,769 B1 | * | 1/2005 | Gandarias | 600/189 |
| 2001/0050082 A1 | * | 12/2001 | Christopher | 128/207.15 |
| 2003/0163068 A1 | | 8/2003 | Kang | |
| 2003/0220556 A1 | | 11/2003 | Porat et al. | |
| 2004/0095464 A1 | * | 5/2004 | Miyagi et al. | 348/65 |
| 2004/0237311 A1 | * | 12/2004 | Brown et al. | 30/141 |

OTHER PUBLICATIONS

B&B Straw Pack Co., Ltd. "Specification". Nov. 25, 2003. B&B Straw Pack Co., Ltd. pp. 1-2. (Available online at <http://web.archive.org/web/20031125201924/http://www.thaistraw.com/spec_eng.htm>).*
Brodsky, Jay, et al. "Tracheal diameter predicts double-lumen tube size: A method for selecting left double-lumen tubes." 1996 Anesth Analg. 82. pp. 861-864.*
Jack J. Jiang et al. "A Methodological Study of Hemilaryngeal Phonation", laryngoscope 103: Aug. 1993, pp. 872-882.
J. Schweinfurth, MD "Iatrogenic Vocal Fold Scar" retrieved from www.eMedicine.com/ent/topic607.htm on Jun. 22, 2004, 8 pages.

* cited by examiner

*Primary Examiner*—Max Hindenburg
*Assistant Examiner*—John Pani
(74) *Attorney, Agent, or Firm*—Fish & Richardson P.C.

(57) ABSTRACT

An apparatus for causing air flow to vibrate a selected tissue includes a tube and a deflector. The tube defines a passage for guiding air flow from an inlet to an outlet thereof. The deflector is disposed to receive the air flow from the outlet of the tube. The configuration of the deflector is such as to channel air flow from the outlet past the selected tissue. This causes vibration of the selected tissue.

15 Claims, 9 Drawing Sheets

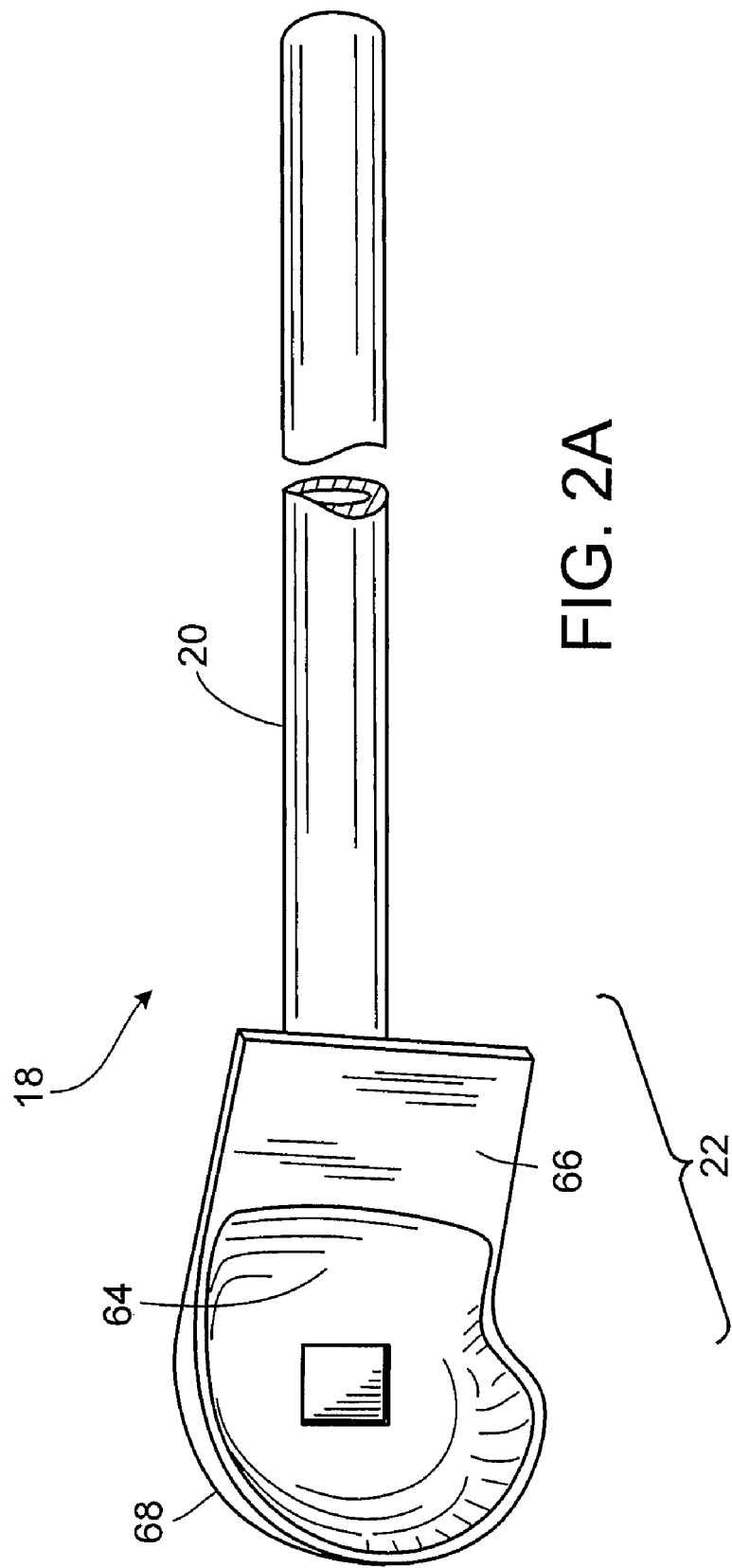

AERODYNAMIC TISSUE DRIVER

TECHNICAL FIELD

This invention relates to devices for assessment of tissue pliability and in particular, to the assessment of vocal fold and skin pliability.

BACKGROUND

The vocal folds, because of their position in the airway, play a vital role in speech, swallowing, and breathing. In order to perform these functions normally, the laryngeal muscles must be able to open and close the folds. In addition, the folds must have the proper biomechanical properties to efficiently and effectively control the air stream when used for voice production.

Each vocal fold is composed of a muscle covered by a ligament running the length of the vocal fold and a more superficial, free mucosal edge that vibrates during voice production. The tissues lying above the muscular body of the vocal fold, called the lamina propria, can be separated into discrete layers based on the concentration of elastin and collagen fibers and fiber orientation. The delicate arrangement of the extracellular matrix proteins within the lamina propria permits passive movement of a vocal cover over the body, resulting in the formation of a mucosal wave as air is passed through the glottis. Mobility of these tissue layers influences the fundamental vibration frequency of the vocal folds and directly impacts the voice.

Scar tissue may form in the vocal fold. This scar tissue can cause adhesion of the vocal fold epithelium to the vocal ligament or deeper tissues, effectively eliminating the gelatinous material of the superficial lamina propria at the scar location. Without the gelatinous layer of the lamina propria, a vocal fold is unable to generate a normal mucosal wave during phonation. Such a vocal fold is referred to as "dysphonic."

Patients with dysphonia caused by vocal fold scarring are typically evaluated by indirect laryngoscopy and video stroboscopy, with particular attention paid to vocal fold mobility, glottic closure, and the presence, amplitude, and symmetry of the mucosal wave.

During speech, the mucosal wave is best observed by illuminating the vocal folds with evenly-spaced light pulses from a strobe light in a technique know as stroboscopy. If the pulsation frequency matches the fundamental vibration frequency of the vocal folds, then the folds will appear stationary even though they are vibrating. If, however, the strobe's pulsation frequency is slightly offset from that of the vocal folds, then the folds will appear to move in slow-motion. The visual appearance of the vocal fold mucosal wave when thus illuminated is a diagnostically important aspect of vocal fold assessment.

Injection of gelatinous material into the superficial lamina propria to treat vocal fold scarring is best performed when the patient is under general anesthesia. The targeted layers of vocal fold are thin and delicate, and must be stationary to ensure accurate injection without tissue trauma. The accuracy of the injection is increased when the surgeon has a direct, magnified view of the injection site through a glottiscope.

Surgeons who inject material into scarred vocal folds to restore pliability would benefit from feedback about how each injection made during the procedure affects vocal fold biomechanical properties. Unfortunately, glottiscope placement is invasive and requires general anesthesia. Under these circumstances, it is impractical to remove the glottiscope and awaken the patient between each intraoperative manipulation in order to ask the patient to phonate.

SUMMARY

In one aspect, the invention includes an apparatus for causing air flow to vibrate a selected tissue, the apparatus includes a tube defining a passage for guiding air flow from an inlet to an outlet thereof. A deflector is disposed to receive the air flow from the outlet. The configuration of the deflector causes channeling of the air flow from the outlet past the selected tissue. This causes the selected tissue to vibrate.

In one embodiment, the deflector includes a cup portion having a rim shaped to conform to tissue proximate to the selected tissue. The cup portion and the tissue proximate to the selected tissue define a chamber for receiving air from the outlet. The cup portion can be made of a variety of materials, such as gold, silver, or surgical steel. In some embodiments, the geometry of the cup portion seals a volume adjacent to a vocal fold. In other embodiments, the geometry of the cup portion seals a volume adjacent to a region of skin surface.

Embodiments of the invention include those in which the cup portion has One geometry of the cup portion a back edge and a front edge, the back edge having a radius-of-curvature greater than a radius-of-curvature of the front edge. Other embodiments include those in which the cup portion has a rim shaped to seal a volume adjacent to a vocal fold.

The deflector can include a flat portion disposed for placement across from the selected tissue and separated therefrom by a gap through which air escapes from the chamber. The deflector can be welded to the tube or it can be integral with the tube.

The apparatus can also include a camera disposed to view the vibrating tissue, and a computer in data communication with the camera, the computer being configured for video stroboscopy. Or, the apparatus can include a microphone disposed to receive an acoustic signal from the vibrating tissue.

In other embodiments, the apparatus also includes a measurement port in fluid communication with the lumen of the tube, the measurement port providing an opening for measurement of a property of air in the tube.

In another aspect, the invention includes a method for assessing mechanical properties of a selected tissue by defining an expansion chamber adjacent to the selected tissue, passing pressurized air into the expansion chamber, and providing an opening through which the pressurized air can escape the expansion chamber, the opening being disposed such that, while escaping from the expansion chamber, air passes by the selected tissue, thereby causing the selected tissue to vibrate.

The tissue whose mechanical properties are to be assessed can be any tissue, including in particular vocal fold tissue and skin.

In one practice, the method includes measuring acoustic waves generated by the vibrating tissue. Other practices include illuminating the vibrating tissue with a stroboscope, determining a fundamental vibration frequency of the selected tissue, and/or determining a phonation threshold pressure of the selected tissue.

These and other embodiments may have one or more of the following advantages. An aerodynamic tissue driver enables intraoperative stroboscopy of vocal fold vibration in the anesthetized patient. The aerodynamic tissue driver enables experimental control of subglottic pressure during phonation. The aerodynamic tissue driver also enables simultaneous stroboscopy and measurement of acoustic and aerodynamic variables. The aerodynamic tissue driver enables independent assessment of right and left vocal fold vibration. Since the patient is anesthetized during usage of the aerodynamic tissue driver, the aerodynamic tissue driver enables assessment of vocal fold vibration that is independent of patient behavior such as conscious voice modification. In other applications, the aerodynamic tissue driver can be applied to enable measurement of pliability of other tissues such as skin.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A and 2B are views of aerodynamic tissue drivers for driving the left and right vocal folds, respectively.

Like reference symbols in the various drawings indicate like elements.

DETAILED DESCRIPTION

Figure 1A:
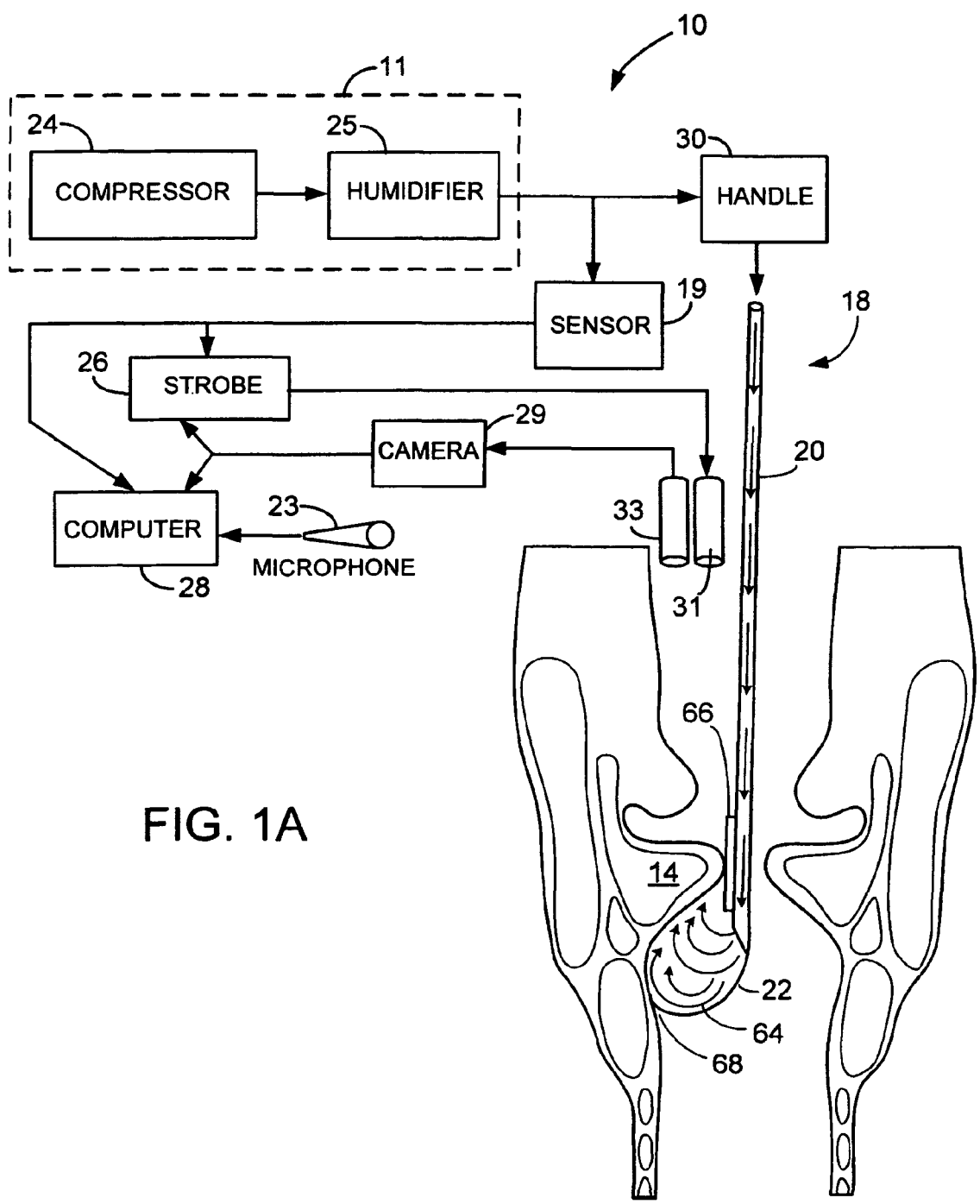
FIG. 1A is a cross-sectional view of an aerodynamic tissue driver.

Referring to FIG. 1A, a system 10 for assessing vocal fold vibration includes a tissue driving subsystem for driving a vocal fold 14 and a diagnostic subsystem for collecting data indicative of the response of the vocal fold 14 to the driving subsystem.

The driving subsystem includes an air supply 11 having a compressor 24, for supplying pressurized air, and a humidifier 25, for adding moisture to the compressed air. A suitable air supply 11 is based on the design of Jiang & Titze "A methodological study of hemilaryngeal phonation," Laryngoscope 1993; 10:872-82, the contents of which are herein incorporated by reference.

The driving subsystem further includes an aerodynamic tissue driver 18 having a tube 20. A proximal end of the tube 20 is connected to the air supply 11. A distal end of the tube 20 is attached a deflector 22, which will be described in more detail below with reference to FIG. 2A. A handle 30, shown schematically in FIG. 1A, is attached near the proximal end of the tube 20 to allow a surgeon to manipulate the position of the deflector 22.

A sensor 19 placed in fluid communication with the interior of the tube 20 allows measurement of characteristics of the air in the tube 20. Exemplary characteristics can include pressure, velocity, temperature, and humidity. Information concerning air pressure is particularly useful for recording how much air pressure is required to initiate vocal fold vibration (phonation threshold pressure). A suitable sensor is available as MPX2010GP from Motorola® of Schaumburg, Ill.

The diagnostic subsystem includes a microphone 23, a strobe light 26, and a video camera 29, all of which are in communication with a computer 28.

The microphone 23 is positioned near the patient's mouth, preferably about fifteen centimeters therefrom. The microphone 23 records sound from the vocal fold 14 as an analog signal. This analog signal is digitized by an A/D converter (not shown). The resulting digitized signal is provided to the computer 28. The computer 28 applies a fast Fourier transform (FFT) to the digitized signal to generate its frequency spectrum, from which a fundamental frequency of the vocal fold 14 is determined.

A first optical relay 31 directs periodic light pulses from the strobe light 26 toward the vocal fold 14. This periodic illumination enables the surgeon to see the mucosal waves. A second optical relay 33 directs light from the vocal fold 14 to the video camera 29, which then provides video information to the computer 28. In addition, the camera 29 sends information about the phase of recorded video frames to the strobe light 26, thereby enabling the strobe flashes to be coordinated with video recording for optimal video quality.

The strobe light 26, computer 28, optical relays 31, 32, and video camera 29 are typically packaged as part of a video stroboscopy unit for measuring the frequency of vocal fold vibrations. An example of a video stroboscopy unit is the Digital Video Stroboscopy System Model 9295 from Kay Elemetrics Corp. of Lincoln Park, N.J.

A high speed video recording system (not shown) can also be used to record motion of the vocal fold 14. Examples of a suitable video system include those that can record digitized images at 2000 frames/second. An example of such a video system is the High-Speed Video System, Model 9700 from Kay Elemetrics® Corp. of Lincoln Park, N.J.

The aerodynamic tissue driver 18 enables real-time assessment of pliability and function of a single vocal fold 14 of an anesthetized patient. This assessment can be performed during phono-microsurgery to evaluate a vocal fold 14 after initial surgical treatment.

FIG. 2A shows the deflector 22 of the aerodynamic tissue driver 18 in more detail. The deflector 22 includes a flat portion 66 and a cup portion 64 distal to the flat portion 66. A tapered bottom portion 68 of the deflector 22 permits the aerodynamic tissue driver 18 to slide into the anterior commissure between the anterior intersection of the left and right vocal folds. The overall shape of the cup portion 64 is selected to form a tight seal against the tracheal wall just below the vocal fold 14.

When properly inserted, the flat portion 66 of the deflector 22 opposes the larynx wall at the level of the vocal fold 14. Meanwhile, the cup portion 64, when seated against the larynx wall below the vocal fold 14, forms a seal. The tracheal wall and the cup portion 64 of the deflector 22 define an expansion chamber having a single narrow opening. The opening is the gap between the flat portion 66 and the vocal fold 14.

The deflector 22 can be cast using metals such as silver, gold, and surgical steel. Other metals or materials can also be used to form the deflector 22. The mold for casting can be made from a wax version of the deflector 22 shaped with reference to an actual vocal fold 14 and trachea wall.

The tube 20 can be a metal tube that is attached to the deflector 22. In other examples, the deflector 22 and the tube 20 can be formed simultaneously using a single mold. This is followed by boring an air passageway through the tube 20.

In operation, pressurized air exits the tube 20 and enters the chamber formed by the cup portion 64 and the tracheal wall. Having no place else to go, this air rushes past the vocal fold 14 as it exits through the gap between the vocal fold 14 and the flat portion 66. This phonates the vocal fold 14.

A particular advantage of the configuration is that only a single vocal fold 14 is driven. As a result, coupling of vibration between vocal folds is avoided.

As noted above, the cup portion 64 has a geometry designed to follow the contour of the subglottal airway below the vocal fold. The trachea walls below the right and left vocal folds become more recessed relative to the medial upper edge of each vocal fold towards the back of the patient. This results in a non-symmetrical cup portion 64. Therefore, there are separate, asymmetrical models of the aerodynamic tissue driver 18: one for driving the right vocal fold and another for driving the left vocal fold. Furthermore, the deflector 22 can be sized to conform to different sizes of vocal folds.

The phonation threshold pressure for phonation of single vocal folds by the aerodynamic tissue driver 18 is consistently higher than the phonation threshold pressure for whole larynx phonation, but shows a similar relative difference for onset versus offset phonation threshold pressure. Experimental alterations of vocal fold properties to simulate pathological conditions result in predictable and reproducible changes in aerodynamic tissue driver phonation measures. The aerodynamic tissue driver 18 can thus characterize altered vocal fold biomechanics following experimental injuries, even if those injuries are not apparent from whole larynx phonation.

Figure 1B:
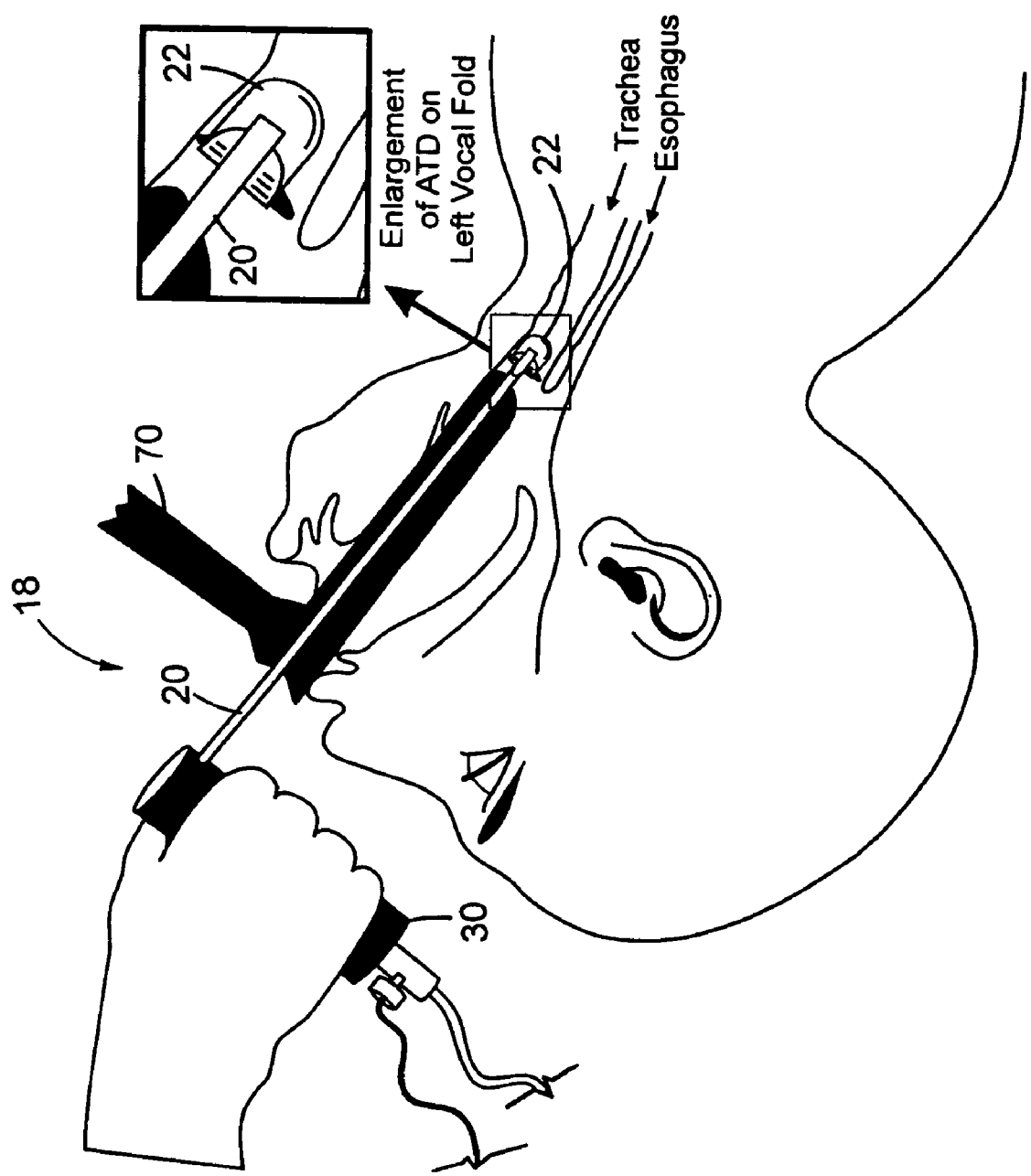
FIG. 1B is a cut-away view of the aerodynamic tissue driver of FIG. 1A.

Referring to FIG. 1B, a surgeon inserts the tube 20 down an anesthetized patient's throat through a surgical glottiscope 70. Following insertion of the tube 20, the surgeon uses the handle 30 to guide the deflector 22 to the correct position against the lateral airway and adjacent to the driven vocal fold 14.

Figure 2B:
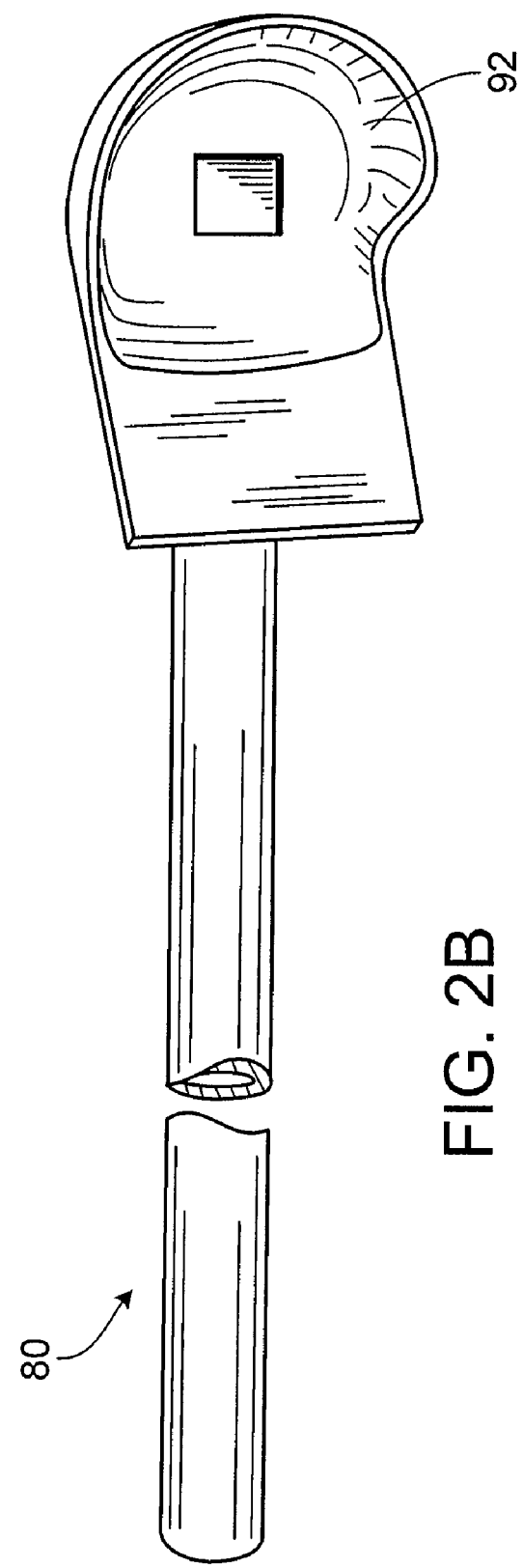

FIG. 2B shows an aerodynamic tissue driver 80 used to drive a right vocal fold. The right aerodynamic tissue driver 80 is a mirror image of the left aerodynamic tissue driver 50 shown in FIG. 2A.

Figure 3:
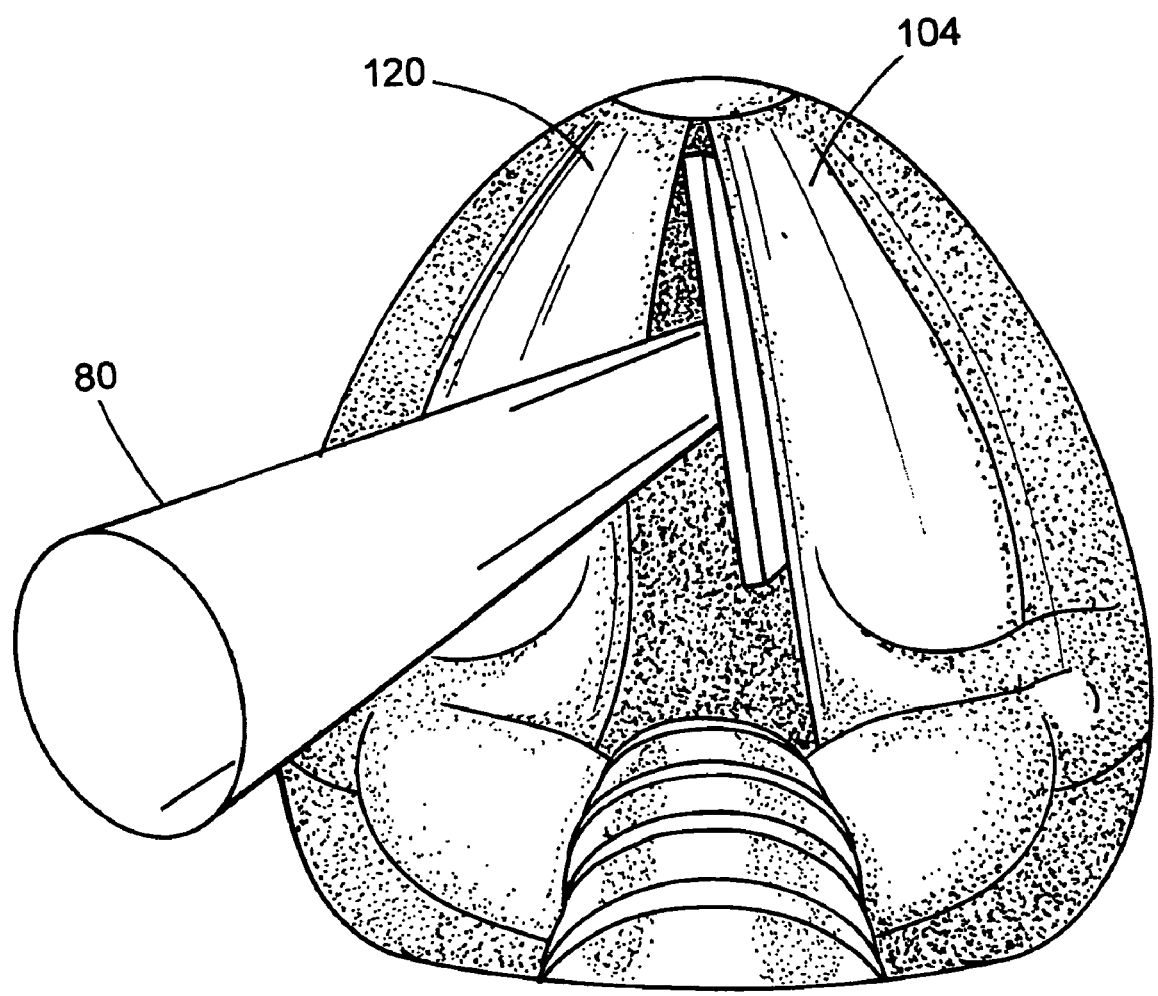
FIG. 3 is a view of an aerodynamic tissue driver being inserted between vocal folds of a patient.

FIG. 3 shows the aerodynamic tissue driver 80 inserted between the left and right vocal folds 120, 104 to contact the lateral tracheal wall below the right vocal fold 104.

Figure 4:
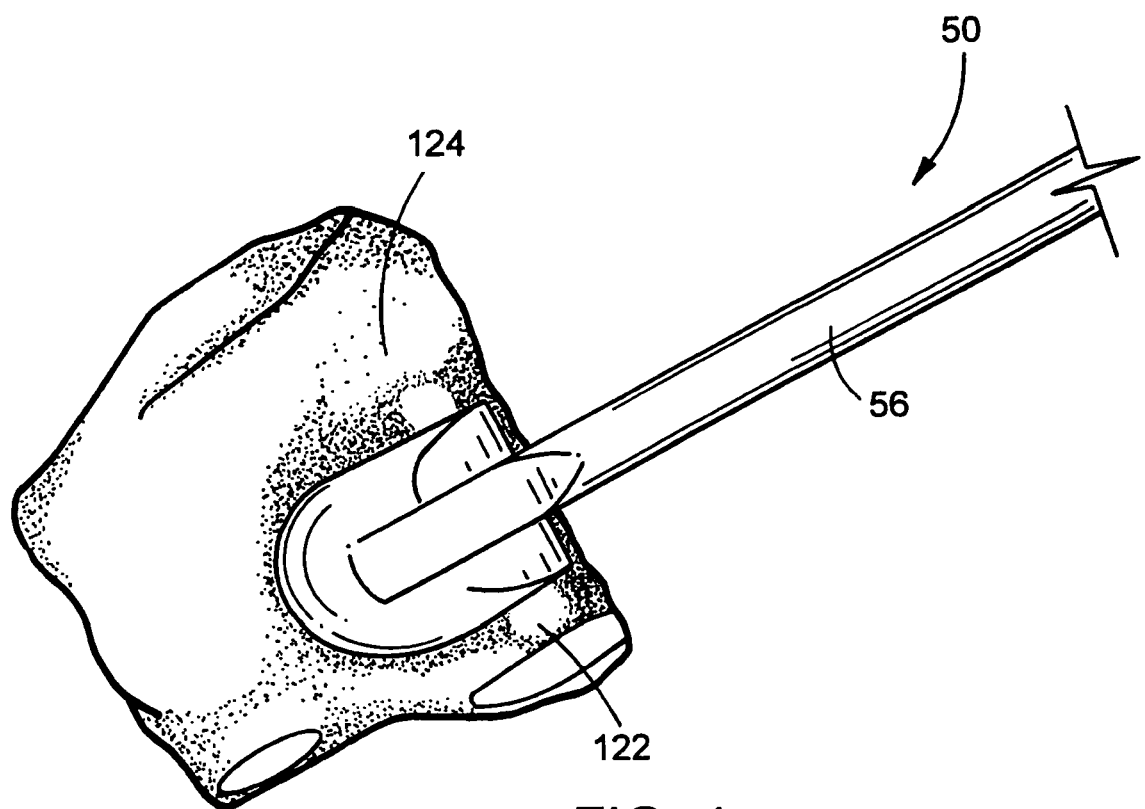
FIGS. 4 and 5 are cut-away views of an aerodynamic tissue driver in position for driving left and right vocal folds respectively.

FIG. 4 shows the left aerodynamic tissue driver 50 placed to phonate the left vocal fold 120. Below the left vocal fold 120 is a tapered front trachea wall section 122 and a more recessed back trachea wall section 124.

Figure 5:
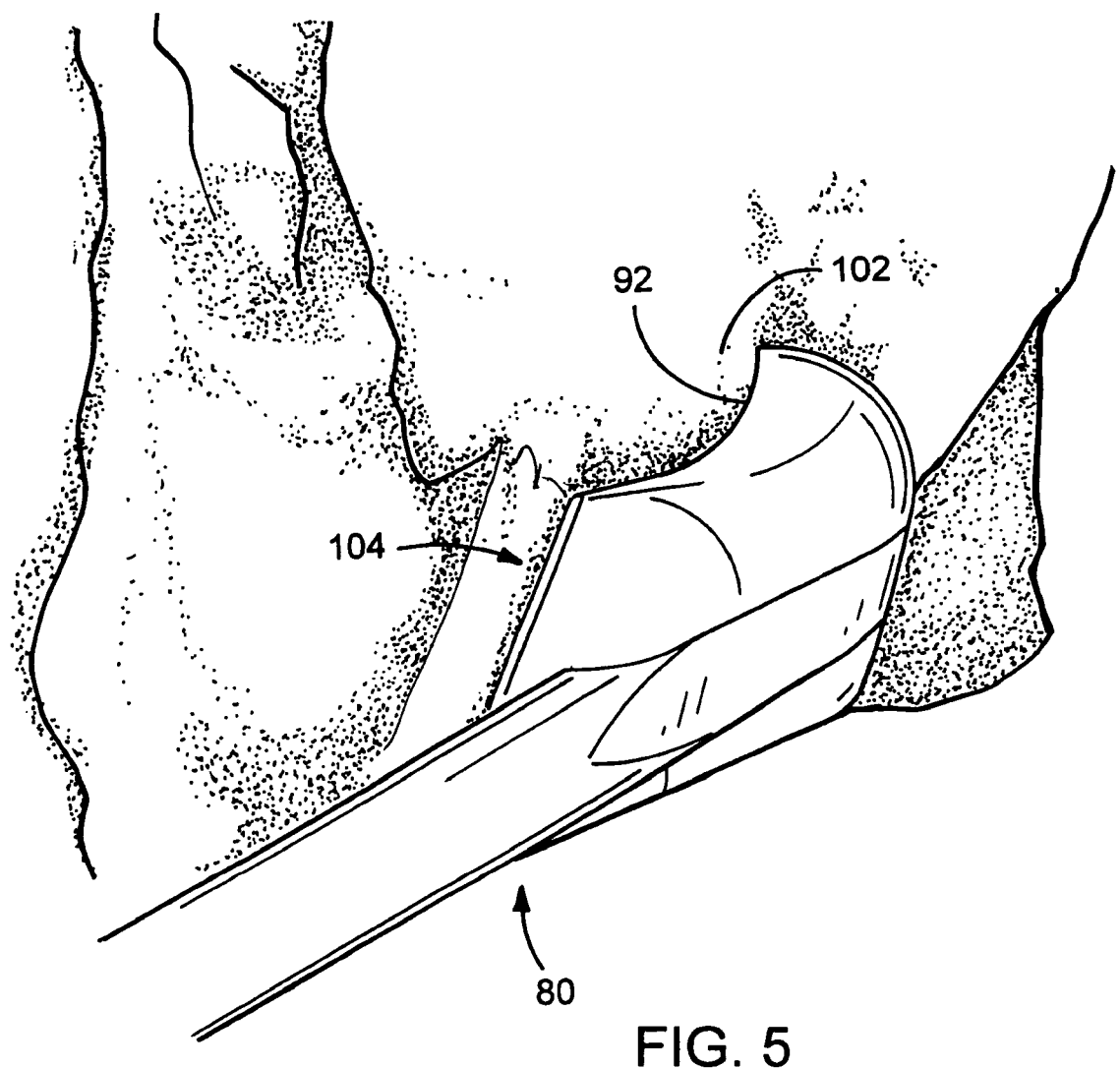

Referring to FIG. 5, the back portion 92 of the right aerodynamic tissue driver 80 is shaped with a deep curvature to conform to the deep curvature of the trachea wall area 102 below the right vocal fold 104.

The general principle of phonating tissue to measure its pliability can be applied to tissues other than the vocal folds. For example, pliability of skin is often of concern to individuals. A quantitative measurement of skin pliability can be useful for determining the effectiveness of skin care products, such as creams. The measurement of skin pliability can also be used to assess a need for plastic surgery, as well as for comparing the differences in pliability before and after the surgery or other treatment.

Figure 6:
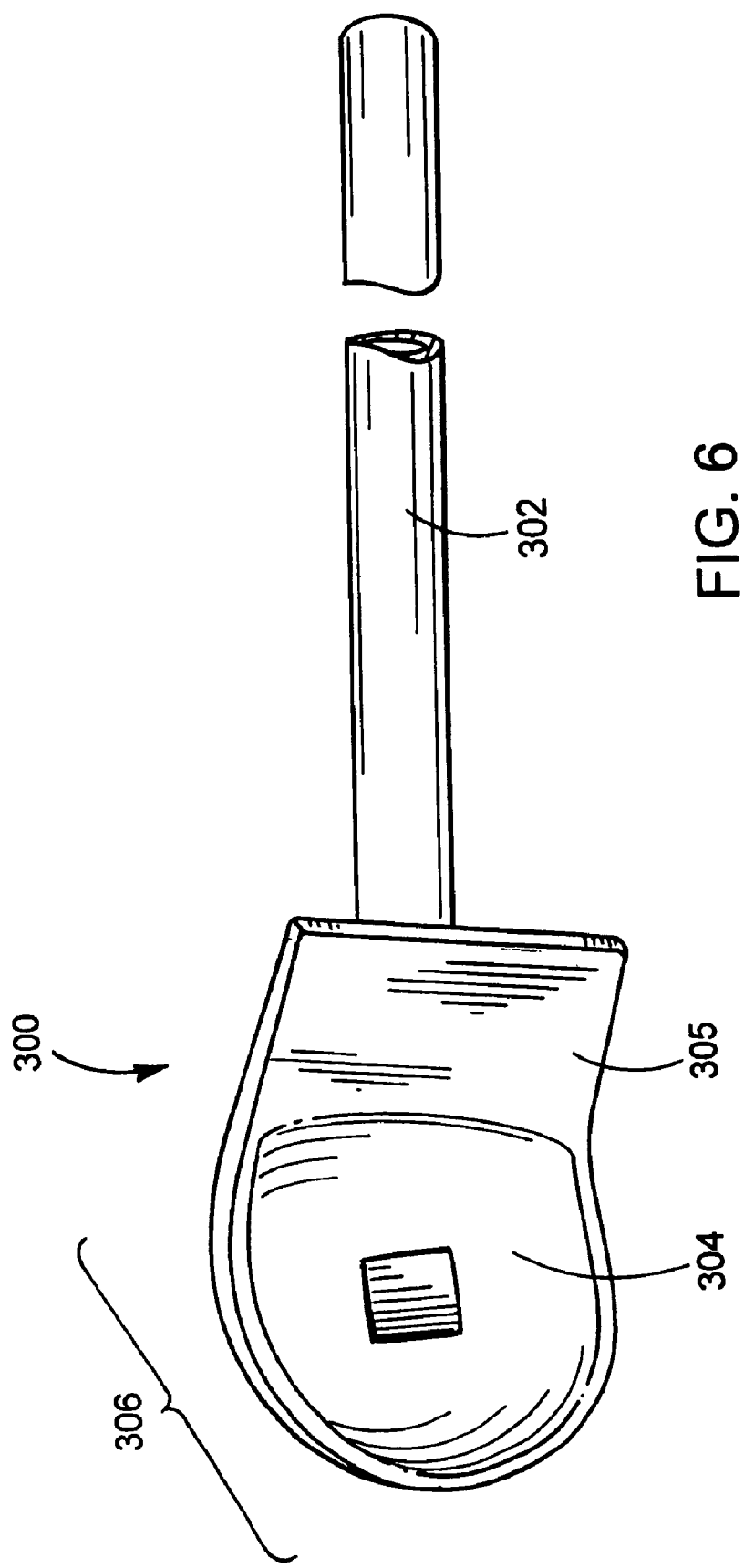
FIG. 6 is a view of an aerodynamic tissue driver for driving skin tissue.

Referring to FIG. 6, an aerodynamic tissue driver 300 can vibrate or phonate skin of a patient to measure pliability of the patient's skin. The aerodynamic tissue driver 300 vibrates or phonates skin by passing air through a tube 302 and into a deflector 304 placed against the skin below a driven portion thereof. The deflector 304 and the skin form an expansion chamber having a narrow opening. Air flows through the tube 302 and into this chamber. The air then escapes from the chamber and flows through a gap between a flat portion 305 and the driven skin. This causes the skin to vibrate.

The aerodynamic tissue driver 300 can be made from different materials. For instance, the deflector 304 can be cast from various metals such as silver, gold, or surgical steel. The tube 302 can be a metal tube connected to an air supply as described previously with respect to FIG. 1A. Similarly, a fundamental frequency of vibration of the skin fold can be measured using a microphone or using video stroboscopy as described previously with respect to FIG. 1A. The fundamental frequency can be related to the pliability of the patient's skin, as can the threshold air pressure required to drive the skin into vibration.

Figure 7:
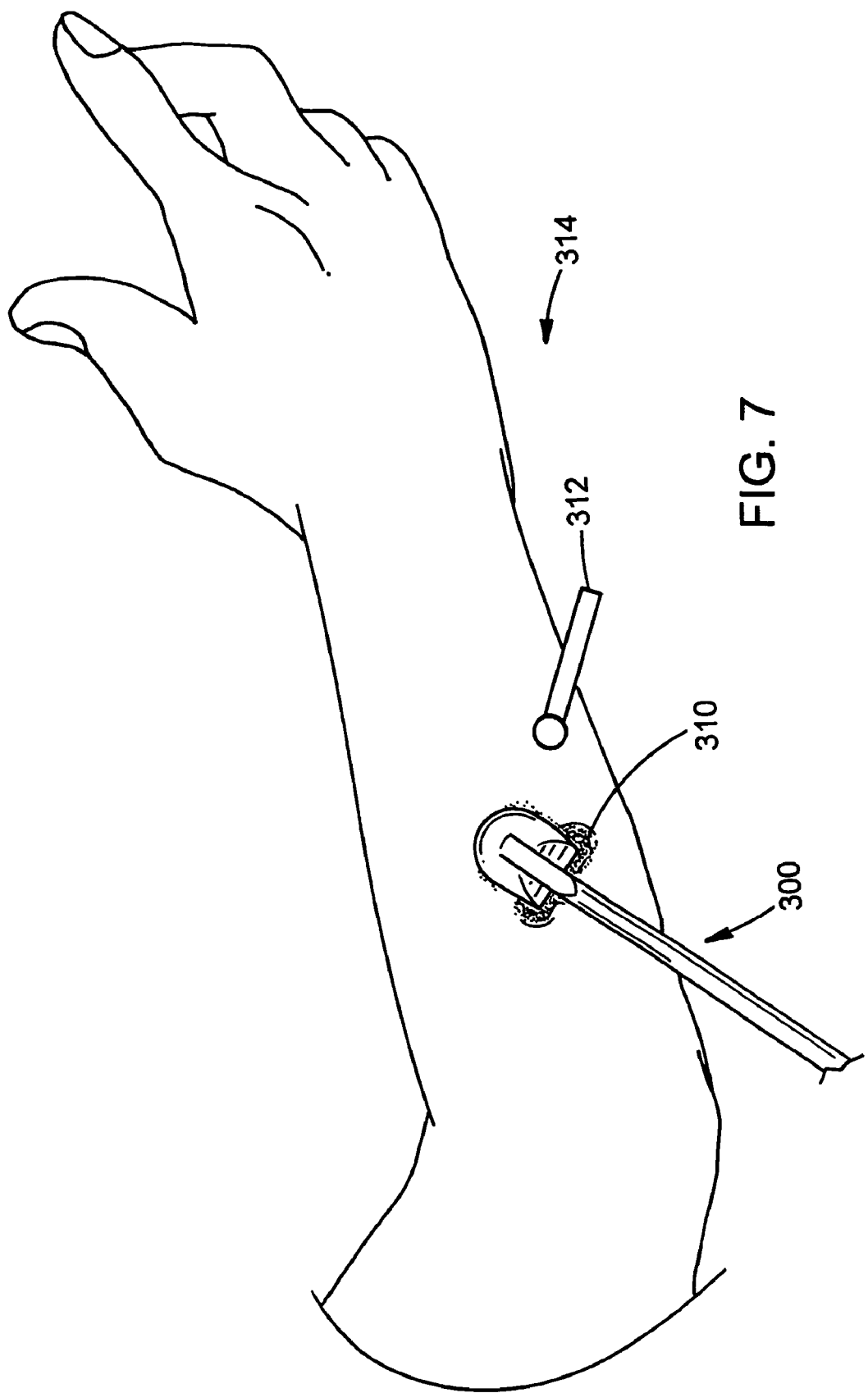
FIG. 7 is a view of the aerodynamic tissue driver of FIG. 6 driving skin on a forearm.

Referring to FIG. 7, the aerodynamic tissue driver 300 is used to phonate a skin fold 310 by firmly pressing the cupped surface 304 against skin below the skin fold 310 to form a seal. The tube 302 is then pressurized. A microphone 312 held close to the exposed skin fold 310 provides a signal representing the resulting vibratory sound. This vibratory signal is then digitized. A computer (not shown) applies a FFT to the digitized signal to generate its frequency spectrum, from which a fundamental frequency of the skin fold 310 is determined. As described previously, a video stroboscopy system 314 can also be used to measure the fundamental frequency of the skin fold 310. In other examples, the aerodynamic tissue driver 300 can be used to phonate a skin fold of a breast, under an arm, and elsewhere on a body. Embodiments of the aerodynamic tissue driver 300 can be sized differently according to sizes of these skin folds.

Only selected embodiments of the invention have been described. Nevertheless, the invention includes embodiments other than those described herein. For example, modifications to the embodiments described herein can be made without exceeding the scope of the invention.

Having described the invention, and a preferred embodiment thereof, what we claim as new, and secured by Letters Patent is:

1. An apparatus for causing air flow to vibrate a vocal fold, the apparatus comprising:
   a tube defining a passage for guiding air flow from an inlet of the tube to an outlet of the tube and having a central axis; and
   a deflector disposed to receive the air flow from the outlet, wherein the deflector is sized to be inserted between human vocal folds and into a trachea,
   wherein the deflector is shaped to contact a lateral tracheal wall below a first vocal fold, when inserted into the trachea, such that air flow from the outlet is channeled past the first vocal fold, thereby causing phonation of the first vocal fold, and
   wherein the deflector comprises:
      an asymmetrical cup portion having a rim shaped to conform to a contour of a subglottal airway, wherein the cup portion is configured to form a seal against the tracheal wall below the first vocal fold, and
      a flat portion extending proximally from the cup portion and adapted to contact the first vocal fold when the deflector is inserted into the trachea, wherein a width of the flat portion perpendicular to the central axis of the tube is selected to enable the flat portion to seal against the first vocal fold and enable the first vocal fold to vibrate against the flat portion.

2. The apparatus of claim 1, wherein the cup portion comprises a back edge and a front edge, the back edge having a radius-of-curvature greater than a radius-of-curvature of the front edge.

3. The apparatus of claim 1, wherein the tube is sized to enable insertion through a glottiscope.

4. The apparatus of claim 1, further comprising a camera disposed to view the first vocal fold, and a computer in data communication with the camera, the computer being configured for video stroboscopy.

5. The apparatus of claim 1, further comprising a microphone disposed to receive an acoustic signal from the first vocal fold.

6. The apparatus of claim 1, wherein the cup portion comprises a metal selected from a group consisting gold, silver, and surgical steel.

7. The apparatus of claim 1, wherein the deflector is welded to the tube.

8. The apparatus of claim 1, wherein the deflector is integral with the tube.

9. The apparatus of claim 1, further comprising a measurement port in fluid communication with the lumen of the tube, the measurement port providing an opening for measurement of a property of air in the tube.

10. The apparatus of claim 1, wherein the deflector is configured to engage the lateral tracheal wall in such a manner as to channel air flow from the outlet in the direction opposite to the direction of air flow exiting the outlet.

11. A method for assessing mechanical properties of a selected vocal fold tissue in a subject, the method comprising:

obtaining the apparatus of claim 1;

positioning the deflector of the apparatus against a lateral tracheal wall of the subject below the vocal fold tissue to define an expansion chamber adjacent to the selected vocal fold tissue;

passing pressurized air into the expansion chamber; and providing an opening through which the pressurized air can escape the expansion chamber, the opening being disposed such that, while escaping from the expansion chamber, air passes by the selected vocal fold tissue, thereby causing the selected tissue to vibrate.

12. The method of claim 11, further comprising measuring acoustic waves generated by the vibrating tissue.

13. The method of claim 11, further comprising illuminating the vibrating tissue with a stroboscope.

14. The method of claim 11, further comprising determining a fundamental vibration frequency of the selected tissue.

15. The method of claim 11, further comprising determining a phonation threshold pressure of the selected tissue.

* * * * *